June 10, 1947 E. S. BOERNER Plant Pat. 738
ROSE PLANT
Filed April 22, 1946
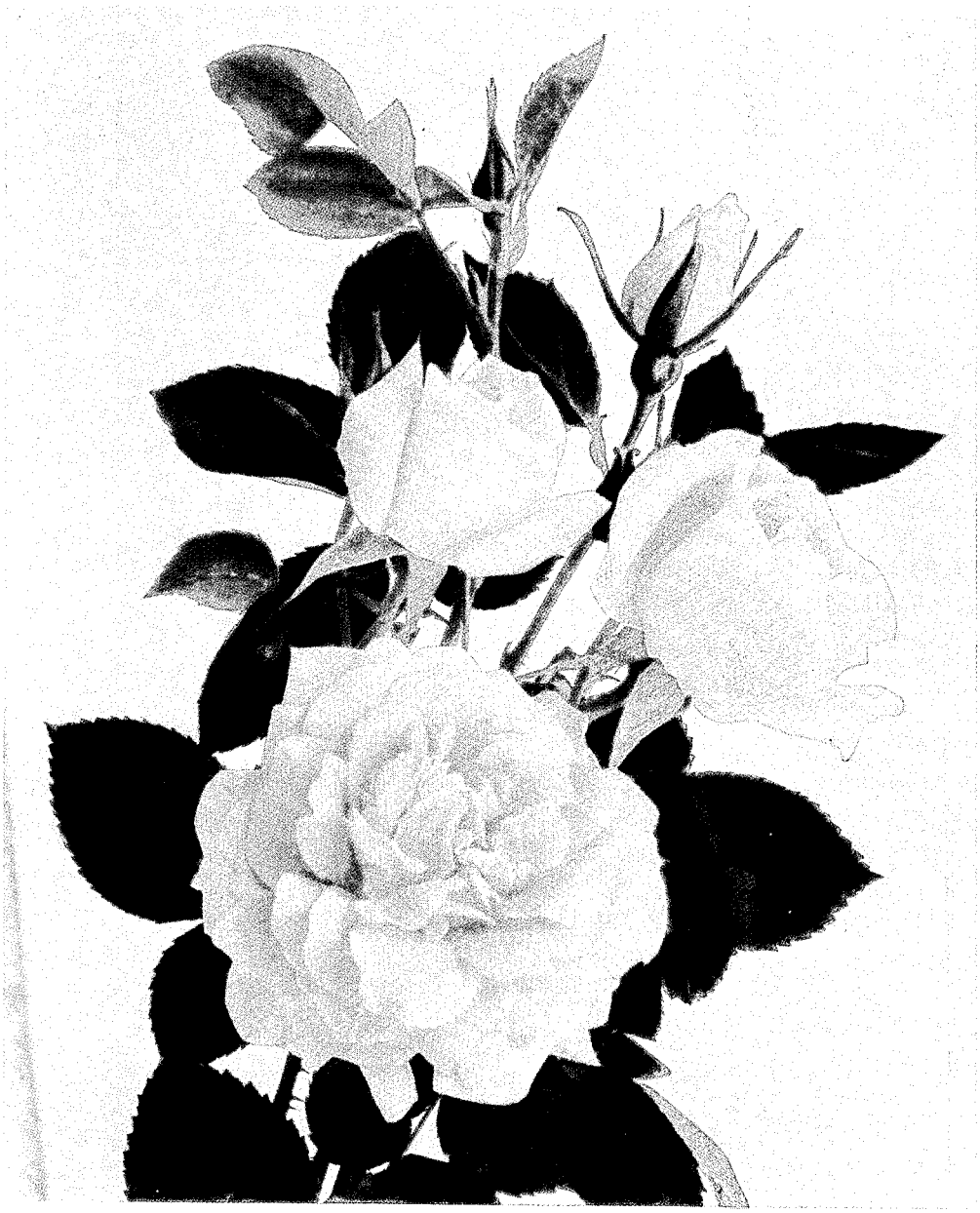
Inventor
E. S. Boerner
By Robert Robb
attorney Patented June 10, 1947

UNITED STATES PATENT OFFICE

738

ROSE PLANT

Eugene S. Boerner, Newark, N. Y., assignor to Jackson & Perkins Company, Newark, N. Y., a corporation of New York Application April 22, 1946, Serial No. 663,867

1 Claim. (Cl. 47—61)

The present discovery relates to a new and distinct variety of rose plant, originating as a sport of "McGredy's Sunset" (Pl. Pat 317), one of the most popular and attractive roses in its class of yellow color.

This new variety, in respect to its general bush habit of growth and foliage characteristics, is quite similar to its parent, but it differs therefrom predominantly as regards the color of the flowers and the number of petals thereof.

Whereas the parent produces flowers of Orange Yellow, those of this sport variety are Rose Doree overlaid with Strawberry Pink, producing in all stages of development a wholly different, more pleasing and attractive color combination.

The parent plant blooms average 25–35 petals while the sport variety herein referred to averages 35 to 40, thereby increasing the doubling effect, without much difference in average size of bloom.

Asexual reproduction of this new variety shows the foregoing characteristics come true to form and are established.

The drawing illustrates a specimen group of this new variety, showing the blooms at different stages of development from bud to full blown flower.

The following is a detailed description of the new variety, the color terminology being in accordance with Ridgway's Color Standard:

Parentage: Sport. *Parent* — "McGredy's Sunset."

Classification: Botanic and commercial—Hybrid tea.

*Flower*

(Observations made in the fields of Jackson & Perkins Company, Newark, New York, in the month of November, 1945.)

Blooming habit: Recurrent—intermittent.

Bud:

*Size.*—Medium.

*Form.*—Ovoid. Is not affected by wet or hot weather.

*Color.*—When sepals first divide—Nopal Red, Plate I. When petals begin to unfurl—Rose Doree, Plate I. When half blown—inside of petals—Geranium Pink, Plate I, with suffusion of Empire Yellows, Plate 4, from base; reverse of petals—Light Orange Yellow, Plate 3.

*Sepals.*—Smooth edge; curl back when petals begin to unfurl. *Color*—outside—Rainette Green, Plate 31; inside—Glass Green, Plate 31.

*Calyx.* — Shape — apple. Size — long. Aspect—smooth. Odor when rubbed—none. Color—Jade Green, Plate 31.

*Peduncle.* — Length — Medium. Aspect — Rough. Color—Garnet Brown, Plate I. Strength—Erect; slender.

*Opening.*—Opens up well. Is not affected by adverse conditions.

Bloom:

*Size.*—Medium. Average size when fully expanded, 4–4½ inches.

*Borne.*—Singly and several together.

*Stems.*—Medium length; strong.

*Form.*—When first open—cupped. Permanence—flattens.

*Petalage.*—Double (full but open center). Number of petals under normal conditions, 35–40.

*Color.* Center of flower—Rose Doree, Plate I, overlaid with Strawberry Pink, Plate I. Outer petals — Geranium Pink, Plate I. Base of petals (aiglet)—Lemon Chrome, Plate 4. Inside of petals—Geranium Pink, Plate I, with suffusion of Empire Yellow, Plate 4, from the base. Reverse of petals—Apricot Yellow, Plate 4. General tonality from a distance—Rose Doree, Plate I, overlaid with Strawberry Pink, Plate I.

*Discoloration.*—General tonality at end of first day—Rose Doree, Plate I, overlaid with Strawberry Pink, Plate I. Second day—Geranium Pink, Plate, overlaid with Strawberry Pink, Plate I. Third day—Geranium Pink, Plate I.

Petals:

*Texture.*—Thick; is not affected by wet or hot weather.

*Appearance.*—Inside—shiny; outside—satiny.

*Form.*—Oval.

*Arrangement.*—Informal (with "rags" in center). Petaloids in center—few; large.

*Persistence.*—Drop off cleanly.

*Fragrance.*—Moderate. Nature—tea (average hybrid tea scent).

*Lasting quality.*—On the plant and as cut flower—long.

Genital organs:

*Stamens, anthers.*—Large; many. Color—Light Cadmium, Plate 4. Arrangement—regular around styles.

*Stamens, filaments (threads).*—Long. Color—Apricot Yellow, Plate 4.

*Pollen.*—Buff Yellow, Plate 4.

*Styles.*—Bunched; uneven length; medium long; heavy.
*Stigmas.*—Picric Yellow, Plate 4.
*Ovaries.*—All enclosed in calyx.

*Plant*

Form: Bush.
Growth: Vigorous; branching.
Foliage: 5–7 leaflets.
*Size.*—Medium.
*Quantity.*—Normal.
*Color.*—New foliage—upper side: Madder Brown, Plate 14, mid-rib, Oil Green, Plate 5; under side: Acajou Red, Plate 13, mid-rib, Oil Green, Plate 5. Old foliage—upper side: Cress Green, Plate 31; under side: Light Cress Green, Plate 31.
*Shape.*—Oval.
*Texture.*—Upper side—Leathery; glossy; under side—rough. Ribs and veins—prominent.
*Edge.*—Serrated (saw toothed).
*Serration.*—Single; small; sharp.
*Leaf stem.*—Light Cress Green, Plate 31. Under side—rough.
*Stipules.*—Medium length; bearded.
*Disease resistance.*—Good.

Wood:
*New wood.*—Color—Madder Brown, Plate 13. Bark—rough.
*Old wood.*—Color—Dull Citrine, Plate 16. Bark—rough.
Thorns (thorns are divided into thorns, prickles, and short needles):
*Thorns.*—Quantity—on main stalks from base and on laterals from stalk—ordinary. Form—narrow base; medium length; hooked downward. Color when young—Garnet Brown, Plate I. Position—irregular.
*Prickles.*—Quantity—on main stalks and on laterals—few. Color—Eugenia Red, Plate 13.
*Short needles.*—Quantity—on main stalks and on laterals—none.

I claim:

A new and distinct variety of Rose plant of the hybrid tea class, characterized as to novelty dominantly by the color combination of its flowers and greater number of petals per bloom as compared with its parent variety, substantially as shown and described.

EUGENE S. BOERNER.